(12) United States Patent
Yamaguchi et al.

(10) Patent No.: US 9,239,304 B2
(45) Date of Patent: Jan. 19, 2016

(54) X-RAY IMAGING APPARATUS

(75) Inventors: Kimiaki Yamaguchi, Tokyo (JP); Toru Den, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 97 days.

(21) Appl. No.: 13/994,654

(22) PCT Filed: Nov. 21, 2011

(86) PCT No.: PCT/JP2011/077439
§ 371 (c)(1),
(2), (4) Date: Jun. 14, 2013

(87) PCT Pub. No.: WO2012/081387
PCT Pub. Date: Jun. 21, 2012

(65) Prior Publication Data
US 2013/0272501 A1    Oct. 17, 2013

(30) Foreign Application Priority Data

Dec. 17, 2010   (JP) ................................. 2010-282233

(51) Int. Cl.
| | |
|---|---|
| *G01N 23/20* | (2006.01) |
| *A61B 6/00* | (2006.01) |
| *G01N 23/04* | (2006.01) |
| *G21K 1/02* | (2006.01) |

(52) U.S. Cl.
CPC *G01N 23/20* (2013.01); *A61B 6/00* (2013.01); *A61B 6/4035* (2013.01); *A61B 6/4291* (2013.01); *A61B 6/484* (2013.01); *G01N 23/04* (2013.01); *G01N 2223/1016* (2013.01); *G01N 2223/313* (2013.01); *G21K 1/02* (2013.01); *G21K 2207/005* (2013.01)

(58) Field of Classification Search
CPC .............. G01N 2223/313; G21K 1/02; G21K 2207/005
USPC ........................................................... 378/62
See application file for complete search history.

(56) References Cited

U.S. PATENT DOCUMENTS

| | | |
|---|---|---|
| 7,492,989 B2 | 2/2009 | Heilmann et al. |
| 2003/0095636 A1 | 5/2003 | Ogura et al. |
| 2007/0183583 A1 | 8/2007 | Baumann et al. |
| 2009/0092227 A1 | 4/2009 | David et al. |
| 2010/0220832 A1 * | 9/2010 | Ning et al. ................ 378/4 |
| 2012/0008747 A1 * | 1/2012 | Roessl et al. ................ 378/87 |

FOREIGN PATENT DOCUMENTS

| | | |
|---|---|---|
| CN | 101011250 A | 8/2007 |
| CN | 101257851 A | 9/2008 |

(Continued)

*Primary Examiner* — Hoon Song
(74) *Attorney, Agent, or Firm* — Canon USA Inc. IP Division

(57) ABSTRACT

The present invention relates to an X-ray imaging apparatus including an X-ray source, a grating that divides diverging X-rays irradiated from the X-ray source, and a detector that detects X-rays which are divided by the grating and pass through a sample. The grating includes a plurality of transparent objects which pass the diverging X-rays and a plurality of opaque objects that shield the diverging X-rays. A focused position at which a plurality of extended lines intersect each other and the X-ray source are arranged in different position. The extended lines are formed by extending center lines which connect a center of the X-ray source side of each of the plurality of opaque objects facing the X-ray source with a center of the detector side of each of the plurality of opaque objects facing the detector.

19 Claims, 13 Drawing Sheets

(56) References Cited

FOREIGN PATENT DOCUMENTS

| | | |
|---|---|---|
| JP | 2010502977 A | 1/2010 |
| JP | 2012-530270 A | 11/2012 |
| JP | 2013-528454 A | 7/2013 |
| RU | 2009109428 A | 9/2010 |

* cited by examiner

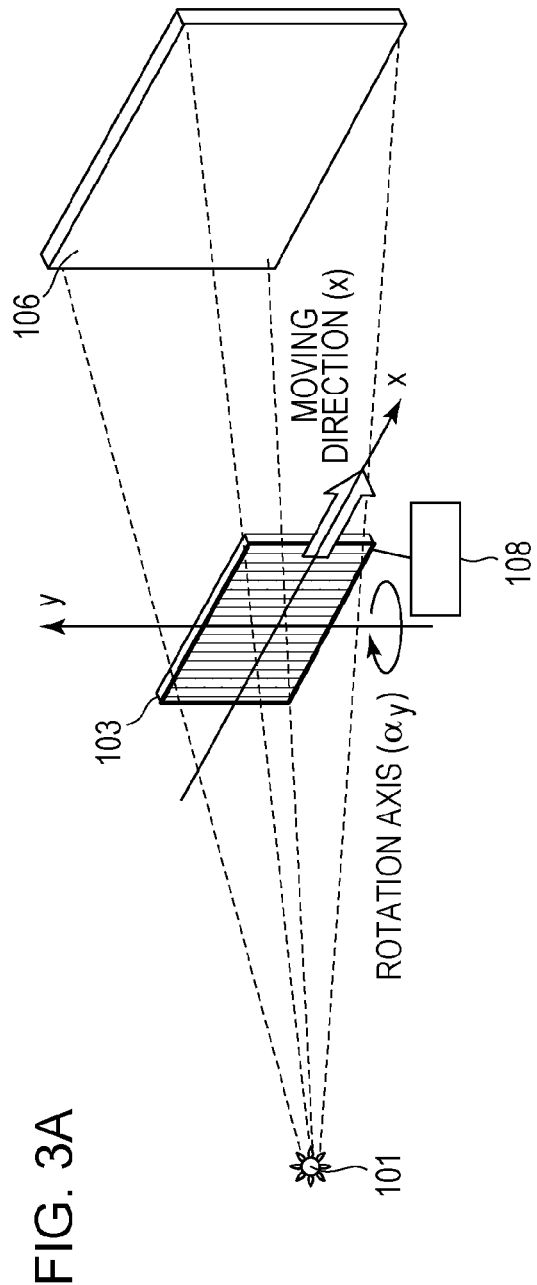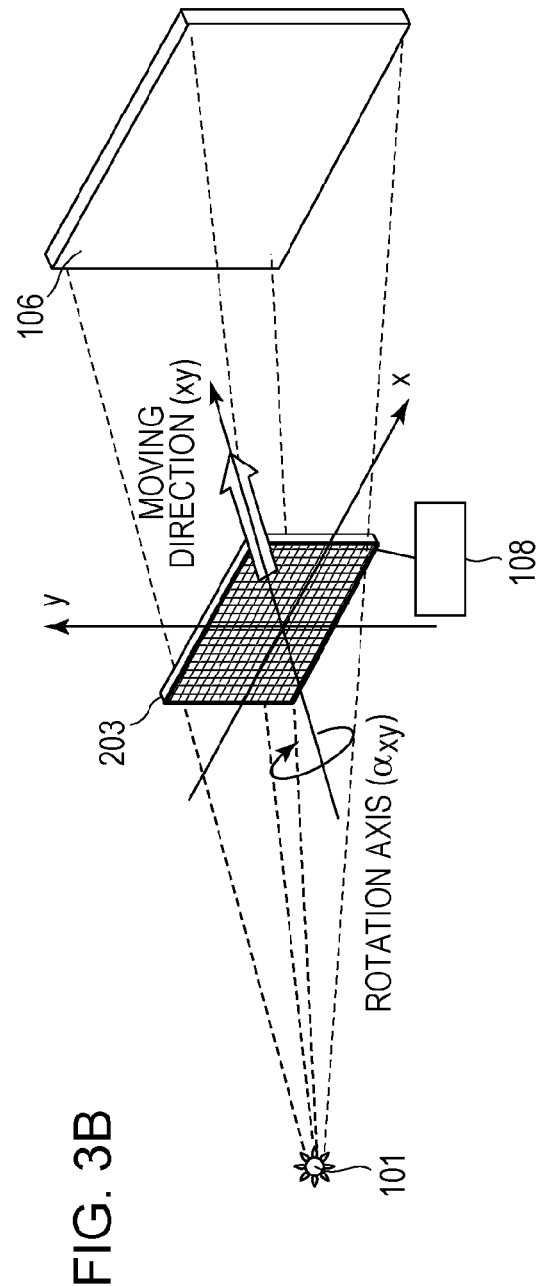

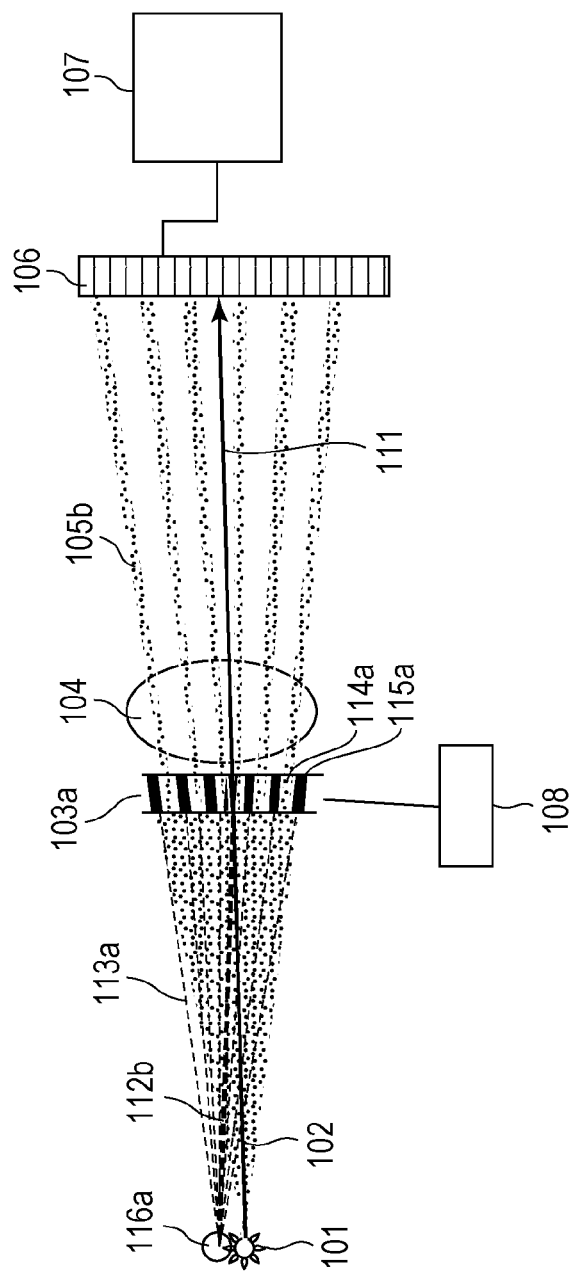

DASHED LINE: APERTURE RATIO: 33% (Al = 33um.Pb = 65um).t = −400um.θ = 0deg
SOLID LINE: APERTURE RATIO: 75% (Al = 75um.Pb = 25um).t = −400um.θ = 8deg

X-RAY IMAGING APPARATUS

TECHNICAL FIELD

The present invention relates to an X-ray imaging apparatus.

BACKGROUND ART

X-ray phase imaging is a method for detecting phase changes of X-rays by a sample and obtaining an image of the sample on the basis of the detection result.

As a method of the X-ray phase imaging, PTL 1 proposes a method for obtaining information related to a phase change of X-rays by detecting the amount of refraction of X-rays by a sample using a fact that X-rays are refracted by a phase change of the X-rays.

The principle of X-ray phase imaging method will be briefly described. In this method, first, X-rays are spatially divided by a grating which includes opaque objects (shield portions) that shield the X-rays and transparent objects (transmission portions) that transmit the X-rays. The divided X-rays become a discrete X-ray beam, the discrete X-ray beams are incident on a sample, and a discrete X-ray beams that are transmitted through the sample are detected by an X-ray detector. Thereby, how much a position of the discrete X-ray beam formed on the X-ray detector is shifted by the sample is known, and the amount of refraction of the X-rays can be obtained from the amount of the shift of the position (hereinafter referred to as "position shift amount"). Hereinafter, unless otherwise described, the position shift amount of the discrete X-ray beam in this description means the amount of positional shift of the discrete X-ray beam on the detector.

When the X-ray phase imaging is performed by the above-described method, generally, the smaller the width of the discrete X-ray beam to be used is, the higher the sensitivity of X-ray phase detection is.

The reason of this will be briefly described. The smaller the width of the discrete X-ray beam to be injected into the detector is, the smaller the intensity of the X-rays detected by each pixel of the detector is. On the other hand, the amount of refraction of X-rays generated by a certain sample does not depend on the width of the discrete X-ray beam, so that the position shift amount of the discrete X-ray beam does not depend on the width of the discrete X-ray beam. Thereby, the smaller the width of the discrete X-ray beam is, the larger the X-ray intensity change which is generated by the positional shift of the discrete X-ray beam and detected by each pixel with respect to the X-ray intensity detected by each pixel of the detector (that is, the X-ray intensity change which is generated by the presence or absence of the sample and detected by each pixel) is. Generally, the larger the X-ray intensity detected by the detector is, the larger the magnitude of the noise is, so that the larger the X-ray intensity change which is generated by the positional shift amount of the discrete X-ray beam and detected by each pixel with respect to the X-ray intensity, the smaller the probability that the X-ray intensity change is buried in the noise. As a result, the phase detection sensitivity of the X-ray imaging apparatus improves.

To reduce the width of the discrete X-ray beam, the width of the transparent objects of the grating is reduced. However, generally, it is difficult to manufacture a grating in which the width of the transparent objects is small. PTL 1 describes an X-ray imaging apparatus which includes two masks and in which the aperture size of masks can be adjusted by adjusting relative positions of the two masks. When the X-ray imaging apparatus is used, it is possible to obtain a discrete X-ray beam having a smaller width by using grating that is conventionally used.

CITATION LIST

Patent Literature

PTL 1 PCT Japanese Translation Patent Publication No. 2010-502977

SUMMARY OF INVENTION

Technical Problem

However, if the width of the discrete X-ray beam passing through a plurality of grating is adjusted by using the grating, a mechanism for adjusting the positional relationship between all the gratings and the detector are required, so that the configuration of the apparatus becomes complicated. Further, generally, when pluralities of gratings are used, the thickness of the transparent objects through which the X-rays pass increases. Even when the transparent objects of the gratings are made of a material with a high X-ray transmittance, such as silicon and aluminum, there is a problem that the intensity of the X-rays passing through the gratings attenuates due to an increase of the thickness of the transparent objects.

Therefore, the present invention provides an X-ray imaging apparatus which uses a grating including transparent objects having a certain width and which can form discrete X-ray beams having substantially the same width as that of discrete X-ray beams formed by using a grating including transparent objects having a width smaller than the certain width of the transparent objects of the grating. As a result, it is possible to obtain substantially the same phase detection sensitivity as that obtained by using a grating including transparent objects having a smaller width.

Solution to Problem

An X-ray imaging apparatus as an aspect of the present invention includes an X-ray source, a grating that divides diverging X-rays irradiated from the X-ray source, and a detector that detects X-rays which are divided by the grating and pass through a sample. The grating includes a plurality of transparent objects through which the cone beam X-rays pass and a plurality of opaque objects that shield the X-rays. A focused position at which a plurality of extended lines intersect each other and the X-ray source are located at positions different from each other. The extended lines are formed by extending center lines which connect a center of each side of the plurality of opaque objects facing the X-ray source with a center of each side of the plurality of opaque objects facing the detector in a direction toward the X-ray source.

Other aspects of the present invention will be apparent from the embodiments described below.

Advantageous Effects of Invention

According to the present invention, it is possible to provide an X-ray imaging apparatus which uses a grating including transparent objects having a certain width and which can form discrete X-ray beams having substantially the same width as that of discrete X-ray beams formed by using a grating including transparent objects having a width smaller than the certain width of the transparent objects of the grating. As a result, it is possible to obtain substantially the same phase detection sensitivity as that obtained by using a grating including transparent objects having a smaller width.

BRIEF DESCRIPTION OF DRAWINGS

FIGS. 3A and 3b are schematic diagrams of moving and rotating directions of the grating according to embodiments and examples of the present invention.

FIG. 4 is a schematic diagram of an X-ray imaging apparatus according to a second embodiment of the present invention.

DESCRIPTION OF EMBODIMENTS

Figure 1:
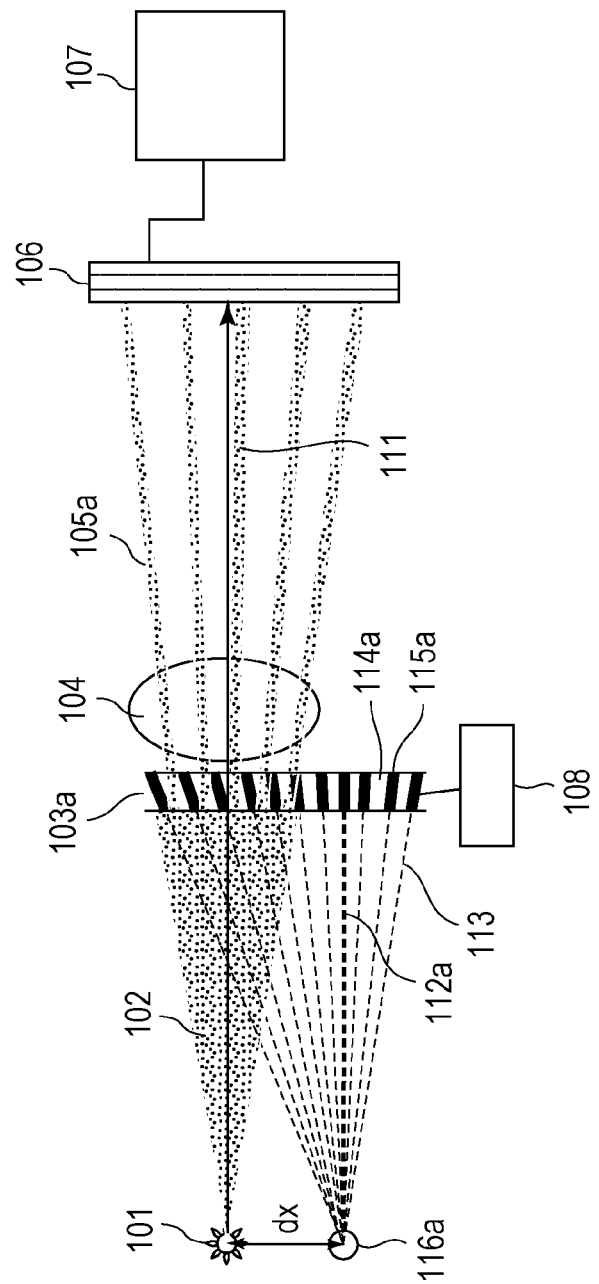
FIG. 1 is a schematic diagram of an X-ray imaging apparatus according to a first embodiment of the present invention.

Hereinafter, embodiments of the present invention will be described with reference to the attached drawings. In the drawings, the same components are denoted by the same reference signs, and redundant description will be omitted.

Embodiments described in this description can form an X-ray beam having a width smaller than a width of transparent objects of a grating by setting an incident angle of X-rays irradiated from an X-ray source to opaque objects of the grating to an angle greater than 0 degrees in an X-ray imaging apparatus. In this description, an angle between a center line of the opaque objects and the X-rays entering the opaque objects is referred to as an incident angle of the X-rays with respect to the opaque objects and represented by θ. The center line of the opaque objects indicates a line connecting the center of the opaque objects facing the X-ray source with the center of the opaque objects facing a detector. The width of the transparent objects indicates a width of the transparent objects on a surface of the grating facing the X-ray source and the width is represented by Ga.

In this description, calculations and models are simplified on two points described below to explain the embodiments.
(1) Luminance in an irradiation direction of the X-rays irradiated from the X-ray source is constant.
(2) Fresnel diffraction when the X-rays pass through the grating is not considered.

First Embodiment

FIG. 1 shows a schematic diagram of an X-ray imaging apparatus according to a first embodiment.

The X-ray imaging apparatus shown in FIG. 1 includes an X-ray source 101, a grating 103a which divides cone beam X-rays 102 irradiated from the X-ray source 101 and forms discrete X-ray beams 105a, a detector 106 which detects the discrete X-ray beams 105a, and a calculation device 107 which performs calculation on the basis of a detection result of the detector 106. The X-ray imaging apparatus also includes a moving/rotating unit 108 of the grating 103a. A sample 104 may be placed between the grating 103a and the detector 106 as shown in FIG. 1, or may be placed between the X-ray source 101 and the grating 103a.

As described above, the X-ray source which generates the cone beam X-rays 102 is used in the X-ray imaging apparatus of the present embodiment. Here, the X-ray source may generate diverging X-rays other than the cone beam X-rays. For example, an X-ray source that generates fan beam X-rays can be used in the present embodiment. In this description, the shortest axis connecting the X-ray source 101 with the detector 106 is referred to as an optical axis 111.

Figure 2:
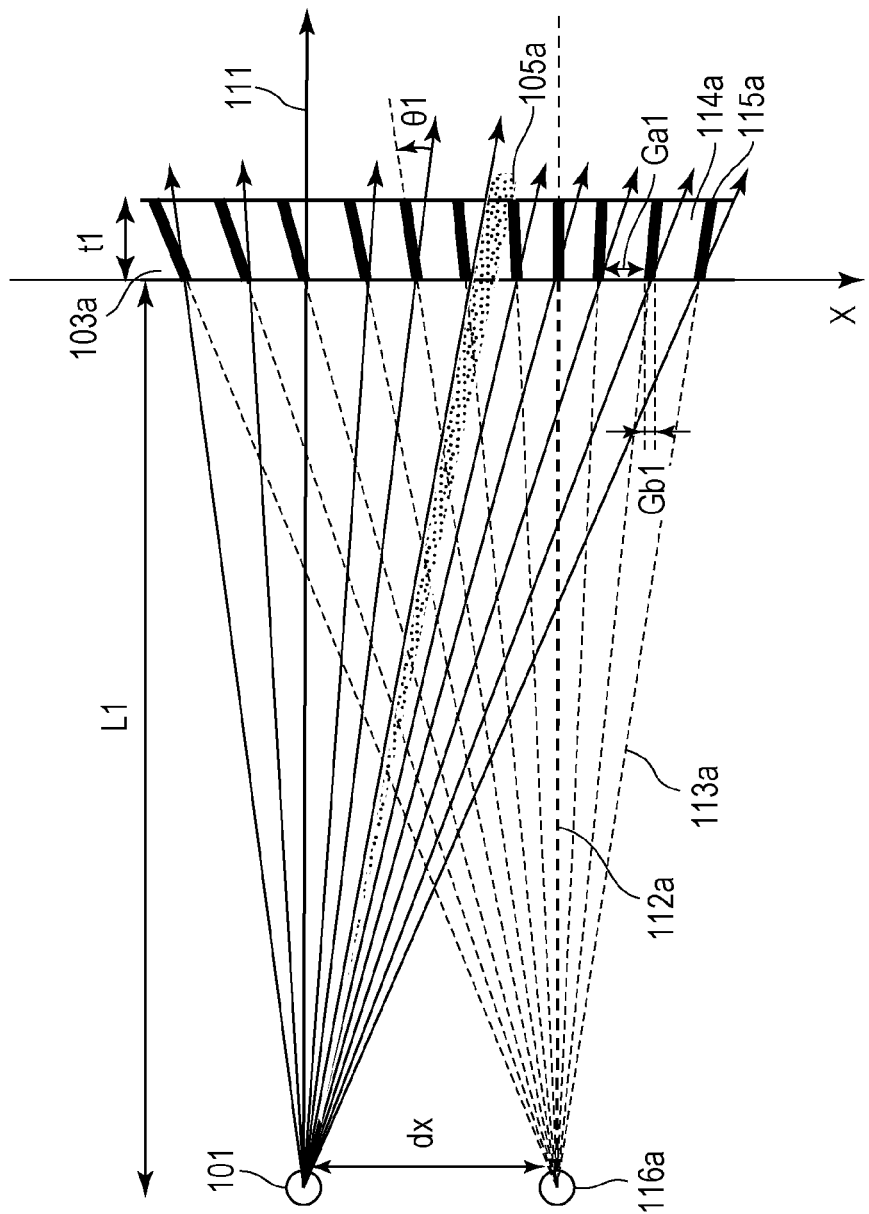
FIG. 2 is a schematic diagram of an X-ray source and a grating according to the first embodiment of the present invention.

The grating 103a has transparent objects 114a that transmit the X-rays and opaque objects 115a that shield the X-rays, so that the grating 103a spatially divides the cone beam X-rays 102 and forms the discrete X-ray beams 105a. FIG. 2 is an enlarged diagram of a portion from the X-ray source 101 to the grating 103a in FIG. 1 and shows a state in which the cone beam X-rays 102 are divided by the grating 103a and the discrete X-ray beams 105a are formed.

The grating 103a used in the present embodiment has the same structure as that of a focused grid (bucky grid) used to eliminate scattered X-rays generated while a phantom is being imaged in a medical X-ray imaging machine. In this structure, the transparent objects 114a made of light elements having a high X-ray transmittance and the opaque objects 115a made of heavy elements having a low X-ray transmittance are alternately arranged. As a material forming the transparent objects 114a, for example, aluminum, paper, or synthetic resin is used. As a material forming the opaque objects 115a, for example, platinum, gold, lead, tantalum, or tungsten is used. The transparent objects may be holes if intervals between the opaque objects can be maintained.

The transparent objects 114a and the opaque objects 115a of the grating 103a are arranged so that a focused position 116a is present in the same way as in the focused grid. However, in this description, an aggregate of positions at which at least two extended lines 113a cross, which are obtained by extending the center line connecting the center of the opaque objects facing the X-ray source with the center of the opaque objects facing the detector in a direction toward the X-ray source, is defined as the focused position 116a.

In this description, a perpendicular line drawn from the surface of the grating 103a facing the X-ray source to the focused position 116a is referred to as a central axis 112a of the grating, and a length of a line segment of the central axis 112a from the surface of the grating 103a facing the X-ray source to the focused position 116a is referred to as a focus distance.

The width of the transparent objects of the grating is represented as Ga, the width of the opaque objects of the grating is represented as Gb, and the thickness of the grating is represented as t. In particular, in the present embodiment, the width of the transparent objects of the grating 103a is represented as Ga1, the width of the opaque objects of the grating 103a is represented as Gb1, and the thickness of the grating 103a is represented as t1. In the grating 103a used in the present embodiment, it is preferred that Ga1 is 10 μm to 180 μm, Gb1 is 20 μm to 180 μm, Ga1+Gb1 is 50 μm to 200 μm, and t1 is 100 μm to 1 mm. However, the widths of the transparent objects and the opaque objects indicate widths of the transparent objects and the opaque objects on the surface of the grating facing the X-ray source. The widths are widths in a direction perpendicular to the central axis of the grating. The thickness of the grating indicates a thickness of the grating in a direction of the optical axis.

If the grating 103a is disposed so that the position at which the X-ray source (X-ray focal point) 101 is disposed corresponds to the focused position 116a, the position of the optical axis 111 corresponds to the position of the central axis 112a. At this time, the cone beam X-rays 102 enter substantially in parallel with the opaque objects 115a, so that the width of the discrete X-ray beam 105a immediately after passing through the grating 103a is substantially the same as the width Ga1 of the transparent objects.

In the present embodiment, as shown in FIG. 2, the grating 103a is moved vertically with respect to the optical axis 111 and disposed. Then, the focused position 116a of the grating is also moved vertically with respect to the optical axis 111. As a result, the cone beam X-rays 102 is incident on the grating at an angle θ1 with respect to the center line of the opaque objects 115a. Then, a part of the cone beam X-rays 102 is shielded by a side surface of the opaque objects 115a, so that the width of the discrete X-ray beam 105a immediately after passing through the grating 103a (the width of the X-ray beam formed by the grating on the surface facing the detector) becomes smaller than the width Ga1 of the transparent objects. The side surface of the opaque objects indicates a surface of the opaque objects in contact with the transparent objects.

As shown in FIG. 3A, an arrangement direction of the transparent objects and the opaque objects of the one-dimensional grating 103a is defined as an x axis and a direction perpendicular to the arrangement direction of the transparent objects and the opaque objects and perpendicular the optical axis 111 is defined as a Y axis. At this time, if the grating 103a is moved in the x axis direction, it is possible to reduce the width of the discrete X-ray beam 105a by a small amount of movement.

At this time, an incident angle θ1 of the cone beam X-rays to the opaque objects located at a position x on the x axis shown in FIG. 2 depends on a parallel movement amount dx of the grating and a distance L1 from the X-ray source 101 to the grating 103a. The incident angle θ1 can be represented by the formula 1. Here, the distance from the X-ray source to the grating indicates a distance from the center of the X-ray source to the surface of the grating facing the X-ray source.

$$\theta1(x) = \arctan(x/L1) - \arctan((x-dx)/L1) \quad \text{(Formula 1)}$$

An actual aperture ratio D of the grating obtained from the incident angle θ of the cone beam X-rays 102 to the opaque objects can be represented by the formula 2.

$$D = (Ga - t \times \tan\theta)/(Ga + Gb) \quad \text{(Formula 2)}$$

The actual aperture ratio D is affected by an angle between the X-rays entering the grating and the center line of the opaque objects 115a.

The width of the discrete X-ray beam formed on the detector by the discrete X-ray beam formed by the grating is represented as Gd, an effective focus size of the cone beam X-rays generated by the X-ray source is represented as f, and a distance from the grating to the detector is represented as L2. Then, the width Gd of the discrete X-ray beam on the detector is represented by the formula 3.

$$Gd = (Ga - t \times \tan\theta) \times (L1 + L2)/L1 + f \times L2/L1 \quad \text{(Formula 3)}$$

As described above, in the X-ray imaging apparatus according to the present embodiment, the smaller the width (Gd1) of the discrete X-ray beam 105a formed on the detector 106 is, the higher the phase detection sensitivity is. It is known from the formulas 1 and 3 that the width Gd1 of the discrete X-ray beam 105a formed on the detector 106 can be reduced by moving the grating 103a by dx.

If the widths Gd of the discrete X-ray beams formed by the grating are not uniform, it may affect imaging of the sample, so that variation of θ of each opaque object should be small. In the X-ray imaging apparatus according to the present embodiment, the nearer to the center of the grating, the larger the θ1 of each opaque object is, and the nearer to an end portion, the smaller the θ1 is. However, when the values of θ1 of each opaque object are within a range of a desired value ±10%, it hardly affects the imaging. The center of the grating here indicates a position at which the x coordinate on the xy plane in FIG. 3A is dx/2. However, even when the variation of θ1 of each opaque object is greater than or equal to ±10%, if the width Gd of each discrete X-ray beam is known in advance, it is possible to correct the variation of the widths of the discrete X-ray beams when the calculation device calculates the phase of the sample.

The amount of movement of the grating can be arbitrarily determined depending on the width Ga1 of the transparent objects 114a of the grating to be used, the width Gb1 of the opaque objects 115a of the grating, the thickness t1 of the grating, a desired width Gd1 of the discrete X-ray beam, and the like. The larger the θ1 is, the smaller the width of the discrete X-ray beam can be. However, if the θ1 is too large, the actual aperture ratio becomes small and a loss of the X-rays increases. Considering the loss of the X-rays, it is preferred that the actual aperture ratio is 5% or more. Therefore, in the present embodiment, considering the widths of the transparent objects and the opaque objects of the grating, the thickness of the grating, and the desired width of the discrete X-ray beam, it is preferred that the θ1 is smaller than 20 degrees, and it is more preferred that the θ1 is smaller than 15 degrees. To reduce the width of the discrete X-ray beam to substantially the same width as that obtained by using a grating having transparent objects with a smaller width, the θ1 is required to be greater than 0 degree. Further, it is preferred that the θ1 is greater than or equal to 1 degree. The actual aperture ratio can be arbitrarily determined depending on a distance between transparent objects adjacent to each other and a desired width of the discrete X-ray beam. Although it is conventionally difficult to manufacture a grating having an aperture ratio of 50% or less, it is possible to manufacture a grating having an actual aperture ratio of smaller than 50% by using the present embodiment. However, the present invention is effective even when the actual aperture ratio of the grating is desired to be set to 50% or more.

The X-ray imaging apparatus of the present embodiment has a structure capable of moving the grating 103a by a moving unit 108 of the grating 103a. Thereby, the amount of movement dx can be changed according to the desired width Gd1 of the discrete X-ray beam. If the X-ray source and the grating are arranged as described above, it is not necessary to provide the moving unit 108.

Although, in the present embodiment, the grating 103a is moved, the incident angle θ1 of the cone beam X-rays 102 to the opaque objects may be adjusted by moving the X-ray source 101. Although the grating 103a of the present embodiment is a one-dimensional grating in which the transparent objects 114a and the opaque objects 115a are one-dimensionally arranged, a two-dimensional grating can also be used. When a two-dimensional grating is used, as shown in FIG. 3B, if a grating 203 is moved in a direction forming an angle of 45° with both the x axis and the y axis on the xy plane, the width of the discrete X-ray beam can be reduced by a small amount of movement.

The discrete X-ray beam passing through the sample 104 is detected by the detector 106. In the present embodiment, the detector 106 is a two-dimensional detector in which image pickup devices which can capture an image of X-rays are two-dimensionally arranged. For example, an FPD (Flat Panel Detector) or a CCD (Charge Coupled Device) that can convert the X-rays into digital signals can be used.

The detection result of the detector 106 is transmitted to the calculation device 107, and an image related to the phase of the sample can be obtained. A calculation to obtain an image related the phase of the sample may be performed by preparing the calculation device 107 separately from the X-ray imaging apparatus and connecting the calculation device 107 to the detector. If necessary, the X-ray imaging apparatus may include a display apparatus (not shown in the drawings) for displaying the image obtained by the calculation of the calculation device 107.

Second Embodiment

FIG. 4 shows a configuration example of an X-ray imaging apparatus according to a second embodiment. The X-ray imaging apparatus of the second embodiment has the same configuration as that of the X-ray imaging apparatus of the first embodiment except for an arrangement of the grating 103a.

Figure 5:
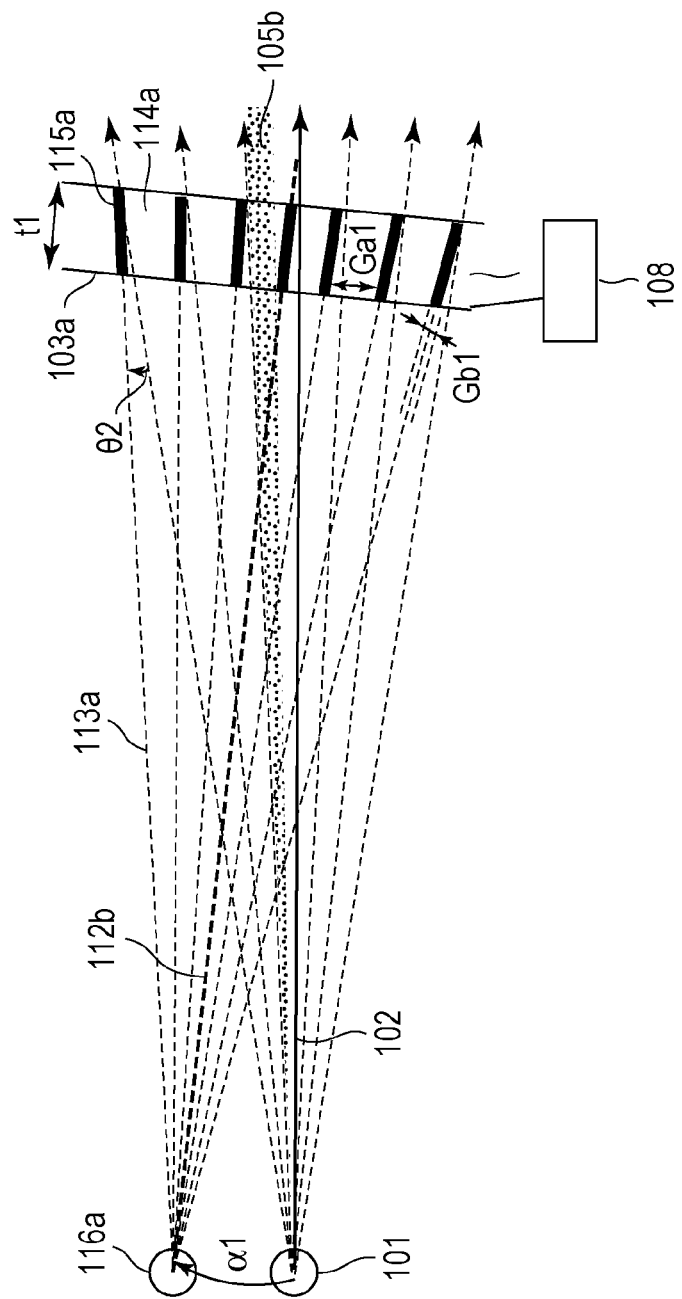
FIG. 5 is a schematic diagram of an X-ray source and a grating according to the second embodiment of the present invention.

FIG. 5 is an enlarged diagram of a portion from the X-ray source 101 to the grating 103a in FIG. 4 and shows a state in which the cone beam X-rays 102 are divided by the grating 103a and the discrete X-ray beams 105b are formed. The grating 103a is the same as the grating 103a used in the X-ray imaging apparatus of the first embodiment and there is the focused position 116a.

The arrangement of the grating 103a of the X-ray imaging apparatus of the second embodiment will be described. First, the grating 103a is arranged so that the focused position 116a of the grating corresponds to the arrangement position of the X-ray source 101. Then, the grating 103a is rotated. Although the grating 103a shown in FIG. 5 rotates around one point on the optical axis, the rotation center of the grating 103a is not necessary to be on the optical axis.

An angle $\alpha 1$ is formed between the optical axis 111 and the central axis 112b of the grating 103a. At this time, the focused position 116a of the grating corresponds to a position obtained by rotating the position at which the X-ray source is arranged around the point on the optical axis (the rotation center of the grating). When the grating is arranged in this way, the cone beam X-rays 102 enter the grating at an angle $\theta 2$ with respect to the center line of each opaque object 115a, and the width of the discrete X-ray beam 105b immediately after passing through the grating 103a becomes smaller than the width Ga1 of the transparent objects. As shown in FIG. 3A, when the one-dimensional grating 103a is rotated around a rotation axis $\alpha y$, it is possible to reduce the width of the discrete X-ray beam 105b by a small rotation angle. At this time, an incident angle $\theta 2$ of the cone beam X-rays 102 with respect to the center line of each opaque object 115a depends on a rotation angle $\alpha$ of the grating 103a, and the incident angle $\theta 2$ can be represented by the formula 4.

$$\theta 2 = \alpha \quad \text{(Formula 4)}$$

Different from $\theta 1$, $\theta 2$ at each opaque object does not vary (when ignoring manufacturing errors). The actual aperture ratio of the grating 103a obtained from the incident angle of the formula 4 can be represented by the formula 2 in the same way as in the first embodiment.

The formula 3 indicates that the width of discrete X-ray beam (Gd2) formed on the detector 106 by the discrete X-ray beam 105b formed by the grating 103a depends on a magnification ((L1+L2)/L1). When the grating is rotated as described in the present embodiment, variation occurs in a distance L1 from the X-ray source to each transparent object 114a and a distance L2 from each transparent object 114a to the detector 106, so that a magnification varies for each discrete X-ray beam. Then, variation occurs in the width formed by each discrete X-ray beam on the detector 106. When $\theta 2$ is small, the variation can be ignored. However, when $\theta 2$ is large, it is necessary to know the width of each discrete X-ray beam 105b in advance. If the width of each discrete X-ray beam 105b is known in advance, it is possible to correct the variation of the widths of the discrete X-ray beams when the calculation device calculates the phase of the sample. To make the widths of the discrete X-ray beams 105b on the detector 106 constant, the detector 106 may be rotated by the same angle in the same direction as the grating 103a.

Although the grating 103a of the present embodiment is a one-dimensional grating, a two-dimensional grating may be used. When a two-dimensional grating 203 is used, as shown in FIG. 3B, if the grating 203 is rotated around a rotation axis $\alpha xy$, it is possible to reduce the width of the discrete X-ray beam 105b by a small rotation angle. The rotation axis $\alpha xy$ is on the xy plane and forms an angle of 45° with both the x axis and the y axis.

The grating 103a may be moved and rotated at the same time to adjust the width of the discrete X-ray beam 105b by combining the first embodiment and the second embodiment. As another method, the grating 103a is rotated around one point on the optical axis, and then the grating 103a is moved in the optical axis direction to shorten or lengthen the distance L1 from the X-ray source to the grating 103a, so that the L1 may be different from the focus distance. However, as a result, variation occurs in $\theta 2$ at the opaque objects, so that, when the L1 is largely different from the focus distance (for example, when the focus distance is out of ±1% range of the L1), it is necessary to know the width of each discrete X-ray beam and calculate the phase of the sample by correcting the widths even when $\theta 2$ is small.

If the X-ray source and the grating are arranged as described above in the same manner as in the first embodiment, it is not necessary to provide the moving unit 108.

Third Embodiment

Figure 6:
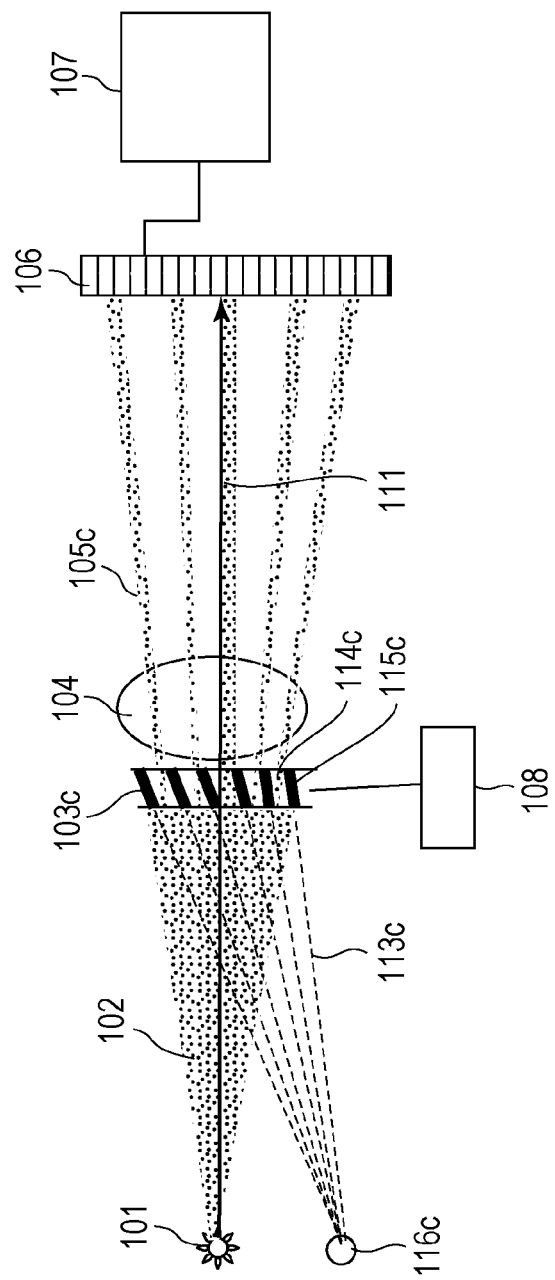
FIG. 6 is a schematic diagram of an X-ray imaging apparatus according to a third embodiment of the present invention.

FIG. 6 shows a configuration example of an X-ray imaging apparatus according to a third embodiment.

The X-ray imaging apparatus of the third embodiment has the same configuration as that of the X-ray imaging apparatus of the first embodiment except for a grating 103c and an arrangement of the grating 103c.

Figure 7:
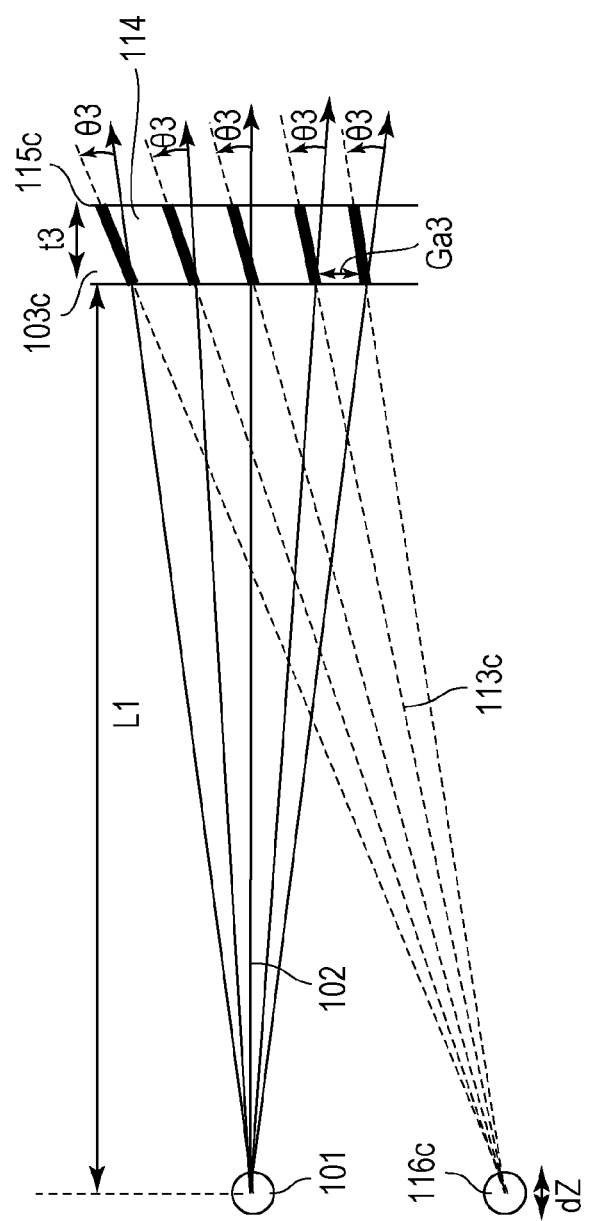
FIG. 7 is a schematic diagram of an X-ray source and a grating according to the third embodiment of the present invention.

FIG. 7 is an enlarged diagram of a portion from the X-ray source 101 to the grating 103c in FIG. 6 and shows a state in which the cone beam X-rays 102 are divided by the grating 103c and the discrete X-ray beams 105c are formed. As shown in FIG. 7, the grating 103c used in the present embodiment includes opaque objects 115c and transparent objects 114c so that all the incident angles of the cone beam X-rays 102 to the opaque objects 115c are the same angle $\theta 3$ when a focused position 116c of the grating and the X-ray source are located at specific positions. In the X-ray imaging apparatus shown in FIG. 7, the incident angles of the cone beam X-rays 102 to the opaque objects 115c are $\theta 3$ when the focused position is located at a position moved from the position at which the X-ray source is located by a predetermined distance in a direction perpendicular to the optical axis. Thereby, the widths of the discrete X-ray beams 105c immediately after passing through the grating 103c are smaller than the width Ga3 of the transparent objects. The incident angles of the cone beam X-rays 102 to the opaque objects 115c are constant, so that the widths of the discrete X-ray beams 105c immediately after passing through the grating 103c can be constant. In the present embodiment, every two extended lines 113c of the center lines of the opaque objects intersect each other, and the focused position 116c which is an aggregate of the intersection points of the extended lines 113c has a linear shape with a specific width dz in the optical axis direction perpendicular to the x axis and the y axis shown in FIG. 3A. Although the dz depends on the size of the grating and the focus distance, generally, the dz is 2 cm or less including a manufacturing error of the grating 103c.

The method of obtaining the amount of refraction by the sample is the same as that in the first embodiment. Although the one-dimensional grating 103a is used in the present embodiment, a two-dimensional grating can also be used in the present embodiment.

If the X-ray source and the grating are arranged as described above in the same manner as in the first embodiment, it is not necessary to provide the moving unit 108.

In the X-ray imaging apparatus of the present embodiment, all the incident angles of the cone beam X-rays 102 to the opaque objects 115c are the same angle θ3 (when ignoring manufacturing errors) and there is no variation in the enlargement ratio of the discrete X-ray beams, so that it is possible to eliminate variation in the widths of the discrete X-ray beams.
Fourth Embodiment FIG. 8 shows a configuration example of an X-ray imaging apparatus according to a fourth embodiment.

In the fourth embodiment, an X-ray imaging apparatus using an X-ray source that generates parallel X-rays will be described.

The configuration of the X-ray imaging apparatus is the same as that of the first embodiment except for the X-ray source and the grating.

Figure 8:
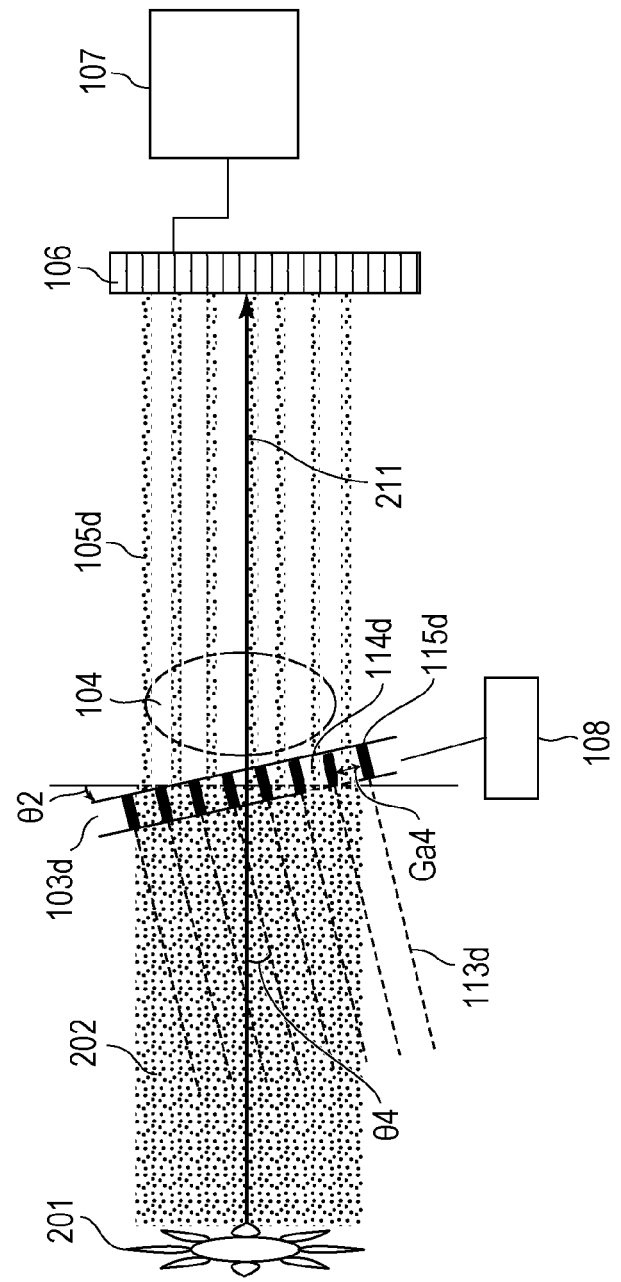
FIG. 8 is a schematic diagram of an X-ray imaging apparatus according to a fourth embodiment of the present invention.

The X-ray imaging apparatus shown in FIG. 8 includes an X-ray source 201, a grating 103d which divides parallel X-rays 202 irradiated from the X-ray source 201 and forms discrete X-ray beams 105d, a detector 106 which detects the discrete X-ray beams, and a calculation device 107 which performs calculation on the basis of a detection result of the detector 106. The X-ray imaging apparatus also includes a moving/rotating unit 108 of the grating 103d.

The grating 103d which spatially divides the parallel X-rays 202 has the same structure as that of a parallel grid used to eliminate scattered X-rays generated while a sample is being imaged in a medical X-ray imaging machine. As shown in FIG. 8, in this structure, the center lines of the opaque objects 115d of the grating 103d are in parallel with each other, and, different from the focused grid, there is no focused position.

The grating 103d shown in FIG. 8 has a structure in which the transparent objects 114a and the opaque objects 115a are vertically provided on the surface of the grating 103d. Thereby, when the parallel X-rays 202 enter the grating 103d, the parallel X-rays 202 enter in parallel with the center lines of the opaque objects 115d and the widths of the discrete X-ray beams 105d immediately after passing through the grating 103d are substantially the same as the widths Ga4 of the transparent objects of the grating 103d. From the state described above, the grating 103d is rotated around a certain point. Although the grating 103d shown in FIG. 8 rotates around the point on the optical axis 211, the rotation center of the grating 103d is not necessary to be on the optical axis. An angle θ4 is formed between the parallel X-rays 202 and the center lines of the opaque objects. The θ4 depends on a rotation angle α2 of the grating 103d and can be represented by the formula 4. The actual aperture ratio of the grating 103d can be represented by the formula 2 in the same way as in the first embodiment.

Figure 9:
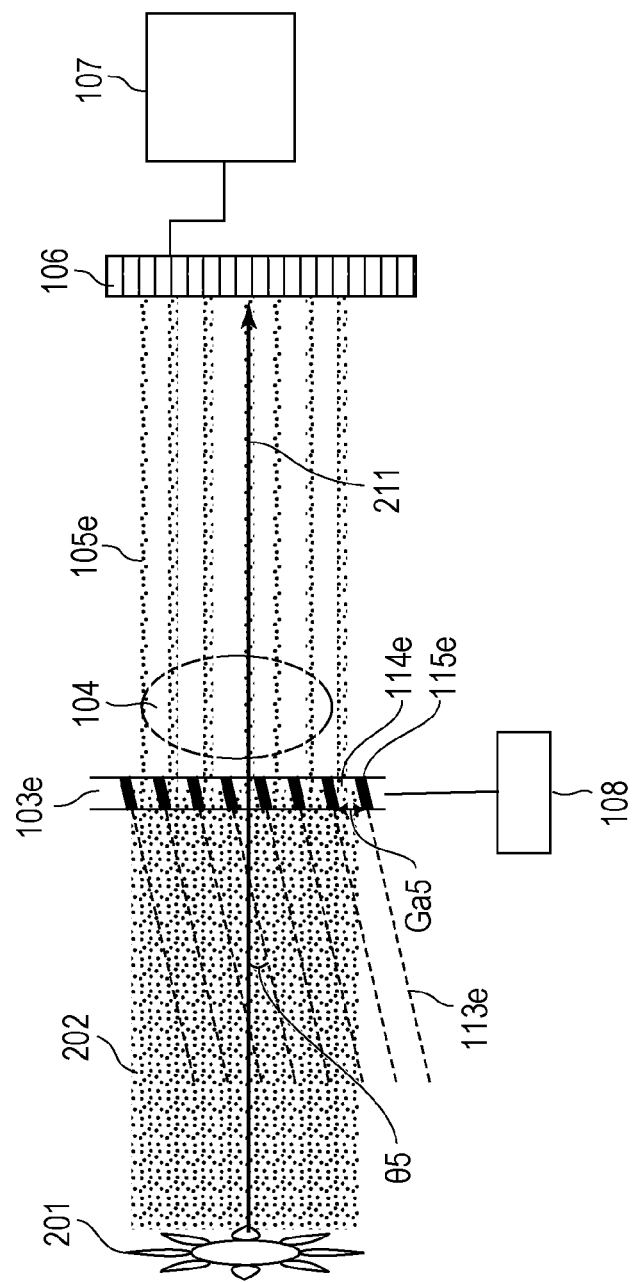
FIG. 9 is a schematic diagram of the X-ray imaging apparatus according to the fourth embodiment of the present invention.

Instead of rotating the grating around the optical axis, as shown in FIG. 9, a grating 103e may be used in which the opaque objects 115e are provided so that the center lines of the opaque objects 115e form a specific angle (90 degrees— θ5) with the surface of the grating 103e. When the grating 103e is used, the incident angle of the parallel X-rays 202 to the opaque objects 115e is θ5, so that the width of the discrete X-ray beam 105e immediately after passing through the grating 103e becomes smaller than the width Ga5 of the transparent objects 114e. In this grating, the opaque objects 115e are in parallel with each other. Although the present embodiment is described on the basis of a one-dimensional grating, a two-dimensional grating may be used.

If the X-ray source and the grating are arranged as described above in the same manner as in the first embodiment, it is not necessary to provide the moving unit 108.

More specific examples of the embodiments will be described.

EXAMPLE 1

In the example 1, a more specific example of the first and the second embodiments will be described.

In the present example, a rotating anticathode X-ray generator of molybdenum, silver, or tungsten target is used as the X-ray source. The cone beam X-rays are generated from the X-ray source and irradiated to the grating.

The grating has aluminum with a width of 70 μm and a thickness of 500 μm as the transparent objects and lead with a width of 30 μm and a thickness of 500 μm as the opaque objects. The focused position is located at a position apart from the grating by 80 cm. The aperture ratio of this grating is 70%. The aperture ratio in this description indicates a ratio of an area of the transparent objects to an area of the grating. The aperture ratio is represented by $Ga/(Ga+Gb) \times 100$ and is not affected by the incident angle of the X-rays to the opaque objects of the grating.

When the grating is arranged so that the focused position corresponds to the arrangement position of the X-ray source, the actual aperture ratio is the same as the aperture ratio of 70%. When the focused position is moved by 2.8 cm in a direction perpendicular to the optical axis by moving the grating, the actual aperture ratio is reduced to 52%, when the focused position is moved by 5.6 cm, the actual aperture ratio is reduced to 35%, and when the focused position is moved by 8.4 cm, the actual aperture ratio is reduced to 17%. Accordingly, the width of the discrete X-ray beam formed by the grating decreases.

Similarly, from a state in which the grating is arranged so that the arrangement position of the X-ray source corresponds to the focused position, if the grating is arranged so that the focused position is located at a position at which the X-ray source is located when the X-ray source is rotated by 4 degrees around an intersection point of the surface of the grating and the optical axis, the actual aperture ratio becomes 35%. At this time, an angle between the central axis of the grating and the optical axis is 4 degrees.

The discrete X-ray beams divided by the grating are irradiated to the sample arranged immediately behind the grating. Further, the amount of refraction of the discrete X-ray beams passing through the sample is detected by arranging a two-dimensional flat panel detector at a position 80 cm behind the grating. The detector is arranged so that each discrete X-ray beam irradiates a plurality of pixels on the detector, and the amount of refraction of the discrete X-ray beams are obtained from a distribution of intensity of the pixels of the detector.

In the present example, the discrete X-ray beams are irradiated to the sample, so that the discrete X-ray beams are irradiated to only a part of the sample and there is a portion of the sample on which the discrete X-ray beams are not irradiated. Information of the portion on which the discrete X-ray beams are not irradiated is not obtained, so that information of the entire sample cannot be obtained by one shot imaging. However, the amount of information of the sample can be increased by moving the discrete X-ray beams or the sample and scanning the sample by the X-rays. When the grating is scanned by the above-described imaging method, it is desired that the detector is scanned by a distance obtained by multiplying the distance scanned on the grating by the enlargement ratio ((L1+L2)/L1).

EXAMPLE 2

In the example 2, the third embodiment will be described more specifically.

The configuration of the X-ray imaging apparatus of the present example is the same as that of the example 1 except for the grating.

The grating has aluminum with a width of 70 μm and a thickness of 500 μm as the transparent objects and lead with a width of 30 μm and a thickness of 500 μm as the opaque objects. The grating is located 80 cm apart from the X-ray source in the same manner as in the example 1.

When the grating is arranged so that the optical axis of the X-ray imaging apparatus passes through the center of the grating, the opaque objects are arranged so that the center lines of all the opaque objects form an angle of 4.2 degrees with the cone beam X-rays entering the grating. In the X-ray imaging apparatus of the present example, the optical axis passes through the center of the grating as described above. As a result, the center lines of the opaque objects form an angle of 4.2 degrees with the cone beam X-rays, so that the actual aperture ratio is 33%. The method of obtaining the amount of refraction of the sample is the same as that in the example 1.

EXAMPLE 3

In the example 3, a method for measuring an X-ray position change in a two-dimensional direction at the same time by using the first embodiment will be described more specifically.

Figure 10:
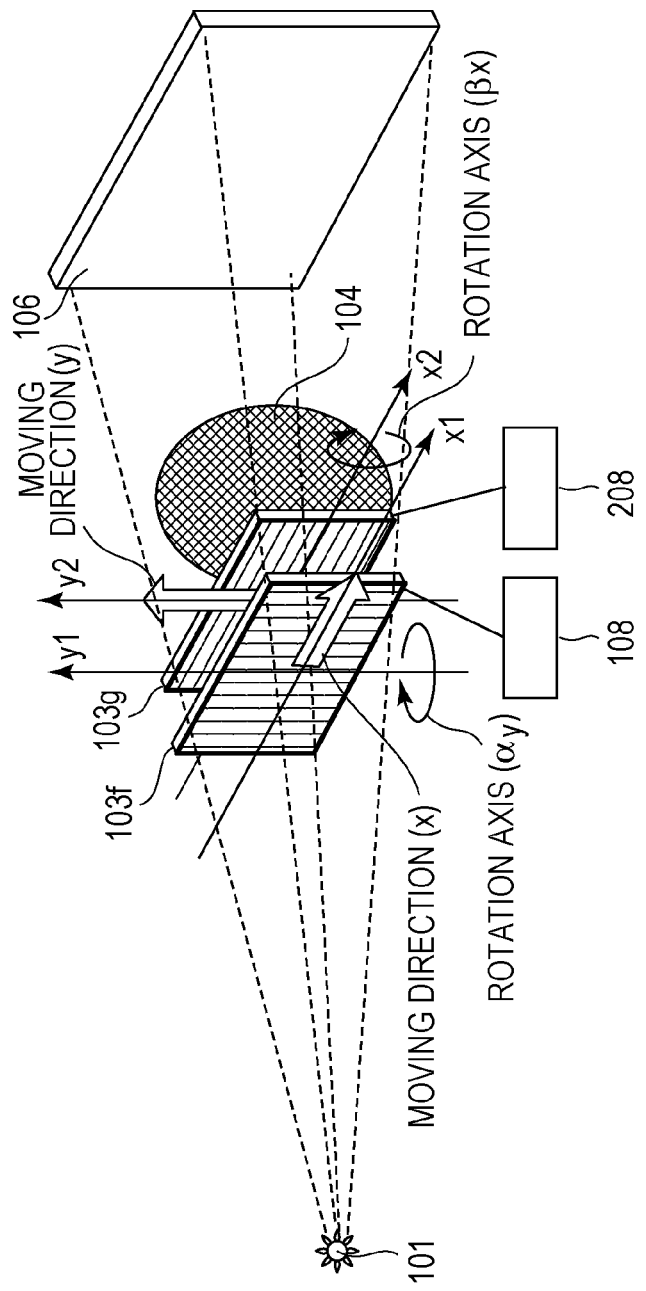
FIG. 10 is a schematic diagram of an X-ray imaging apparatus according to an example 4 of the present invention.

The X-ray imaging apparatus will be described with reference to FIG. 10. In FIG. 10, reference numeral 101 denotes an X-ray source that generates the cone beam X-rays, reference numerals 103$f$ and 103$g$ denote one-dimensional gratings, reference numeral 104 denotes a sample, and reference numeral 106 denotes a flat panel detector. Reference numerals 108 and 208 respectively denote moving/rotating unit of the gratings 103$f$ and 103$g$.

The X-ray source of the present example is the same as that of the example 1. The distance from the X-ray source to the center position between the two gratings is 80 cm.

Both the gratings 103$f$ and 103$g$ of the present example have transparent objects made of aluminum with a width of 70 μm and a thickness of 500 μm and opaque objects made of lead with a width of 30 μm and a thickness of 500 μm. The focused position of each grating is located 80 cm apart from the surface of the each grating. The gratings 103$f$ and 103$g$ are arranged close to each other so that the arrangement directions of the opaque objects and the transparent objects of the grating 103$f$ are perpendicular to those of the grating 103$g$ and the two focused positions of the two gratings are located close to each other as much as possible. Actually, the focused positions of the two gratings are shifted from each other by 500 μm, which is the thickness of the grating. However, such a shift can be ignored as an allowable error. The cone beam X-rays generated from the X-ray source 101 can pass through only portions in which the transparent objects of the grating 103$f$ and the transparent objects of the grating 103$g$ are spatially overlapped with each other, so that the discrete X-ray beams formed by the gratings 103$f$ and 103$g$ have a shape of two-dimensional dot array.

Although the actual aperture ratio is 49% when the X-ray source 101 is located at the focused position of the gratings 103$f$ and 103$g$, when the grating 103$f$ is moved by 2.8 cm in an x1 axis direction and the grating 103$g$ is moved by 2.8 cm in an y2 axis direction, the actual aperture ratio becomes 27%. When the gratings are moved by 5.6 cm, the actual aperture ratio becomes 12%. Similarly, from a state in which the X-ray source 101 is located at the focused position of the gratings 103$f$ and 103$g$, if the grating 103$f$ is rotated by 4 degrees around the rotation axis α$y$ and the grating 103$g$ is rotated by 4 degrees around the rotation axis β$x$, the actual aperture ratio becomes 12%.

Figure 11:
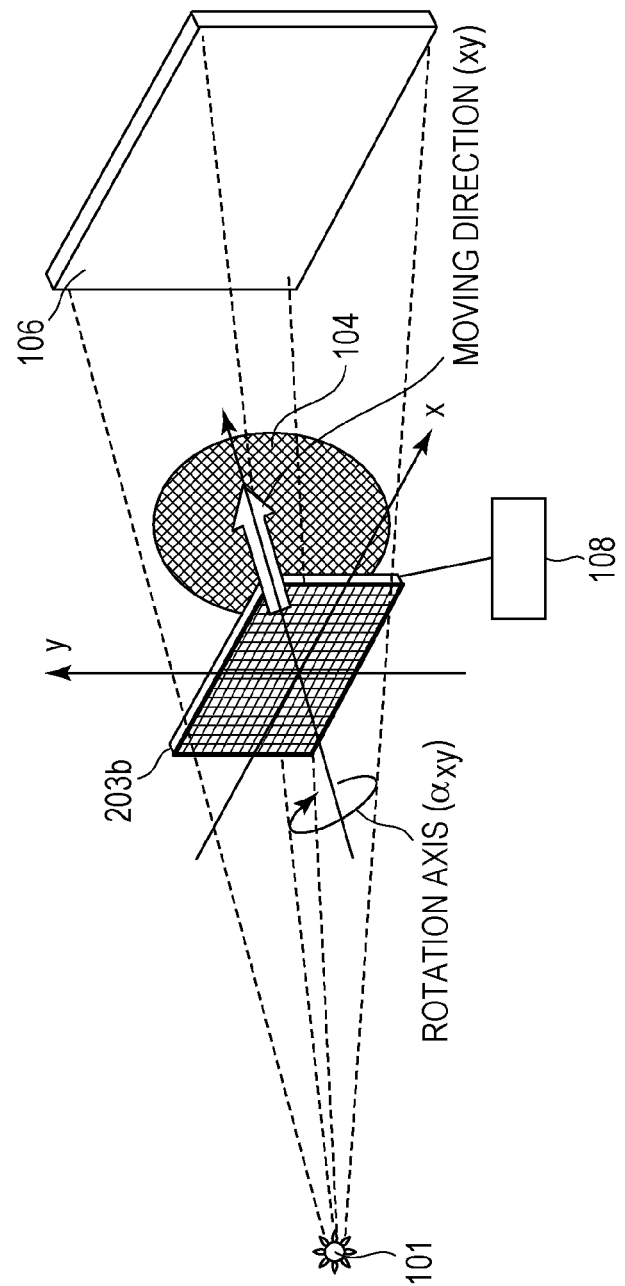
FIG. 11 is a schematic diagram of the X-ray imaging apparatus according to the example 4 of the present invention.

Although, in the X-ray imaging apparatus shown in FIG. 10, the cone beam X-rays are divided into two-dimensional X-rays by using two gratings, the cone beam X-rays may be divided into two-dimensional X-rays by using one grating in which the opaque objects and the transparent objects are arranged in a two dimensional direction. The X-ray imaging apparatus shown in FIG. 11 divides the cone beam X-rays into two-dimensional X-rays by using one two-dimensional grating 203$b$. The two-dimensional grating 203$b$ has a structure in which the gratings 103$f$ and 103$g$ in FIG. 10 are attached to each other in a state in which the arrangement directions of the opaque objects and the transparent objects of the grating 103$f$ are perpendicular to those of the grating 103$g$. When the two-dimensional grating 203$b$ is moved by 4 cm in a direction forming an angle of 45 degrees with both the x axis and the y axis on the xy plane (a direction corresponding to the moving direction in FIG. 3B), the actual aperture ratio can be reduced to 27%. When the two-dimensional grating 203$b$ is moved by 8 cm in the direction, the actual aperture ratio can be reduced to 12%. Further, the actual aperture ratio can be changed by rotating the rotation axis α$xy$ of the two-dimensional grating 203$b$.

To adjust the actual aperture ratio of the gratings 103$f$, 103$g$, and 203$b$, the gratings 103$f$, 103$g$, and 203$b$ may be moved and rotated at the same time. Instead of the gratings 103$f$, 103$g$, and 203$b$, the X-ray source 101 may be moved/rotated.

The method of obtaining the amount of refraction of the sample 104 is the same as that in the example 1.

EXAMPLE 4

In the example 4, a specific example of the fourth embodiment will be described.

The X-rays used in the present example are parallel X-rays.

In the present example, the grating has transparent objects made of aluminum with a width of 70 μm and a thickness of 500 μm and opaque objects made of lead with a width of 30 μm and a thickness of 500 μm. The opaque objects are provided so that the surface of the grating and the center lines of the opaque objects form an angle of 86 degrees, so that an angle between the center lines of the opaque objects and the parallel X-rays is 4 degrees, and the actual aperture ratio is 35%. Further, the grating may be rotated to adjust the actual aperture ratio of the grating from the state described above. The method of obtaining the amount of refraction of the sample in the present example is the same as that in the example 1.

EXAMPLE 5

In the example 5, an intensity distribution of the X-ray beams considering the refraction of the X-rays generated by a refractive index difference between the transparent objects and the opaque objects of the grating and the diffraction generated in the transparent objects of the grating will be specifically described. In the present example, a result of calculation of the intensity distribution of the discrete X-ray beam when using the X-ray imaging apparatus of the first embodiment will be described.

Figure 12:
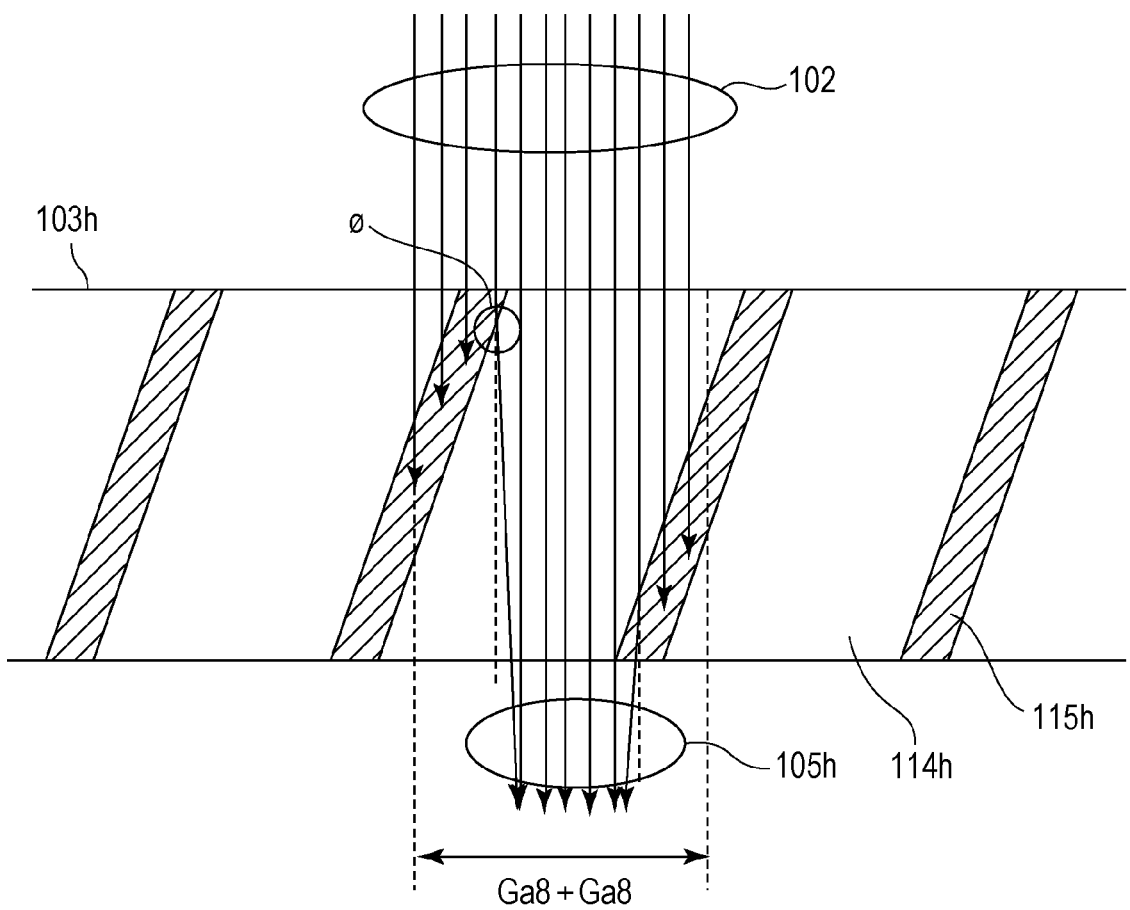
FIG. 12 is a schematic diagram of a grating and a discrete X-ray beam according to an example 5 of the present invention.
Figure 13:
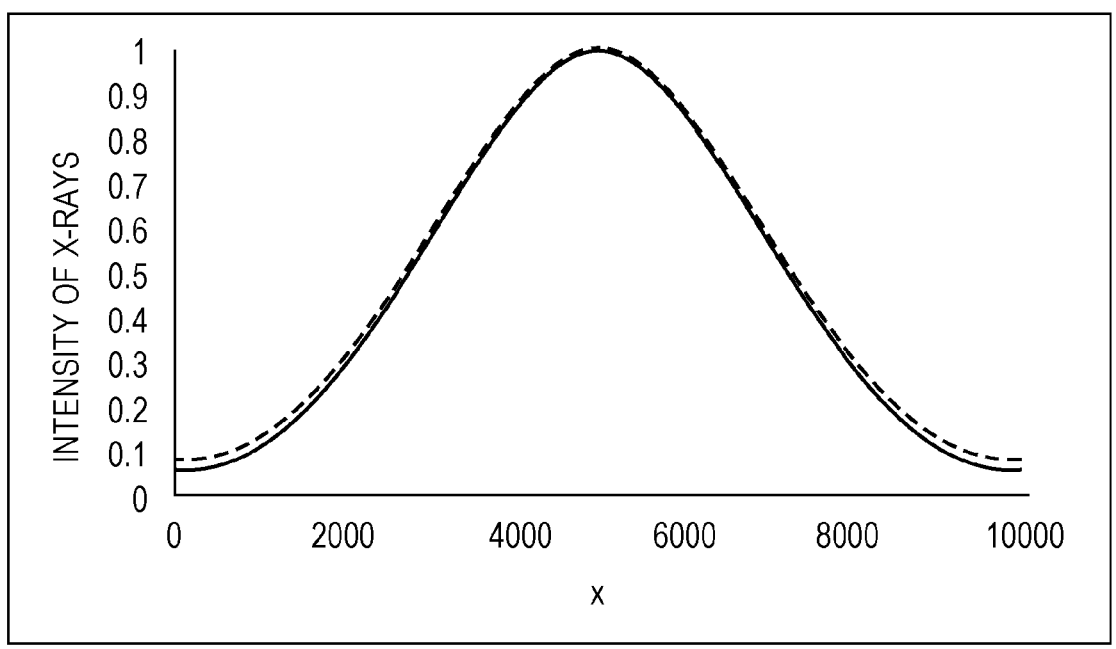
FIG. 13 is an intensity distribution of the discrete X-ray beam formed by the grating according to the example 5 of the present invention.

The formula 3 does not consider the refraction of the X-rays generated by a refractive index difference between the transparent objects and the opaque objects of the grating and the diffraction generated in the transparent objects of the grating. Actually, as shown in FIG. 12, the cone beam X-rays 102 entering the grating 103$h$ are refracted at an interface between the transparent objects 114$h$ and the opaque objects 115$h$ (refraction angle $\phi$). Thereby, the grating 103$h$ has a light collecting effect due to refraction. FIG. 13 shows a calculation result of an intensity distribution of the discrete X-ray beams considering the refraction of the X-rays generated by a refractive index difference between the transparent objects 114$h$ and the opaque objects 115$h$ of the grating 113$h$, the diffraction generated in the transparent objects, and blur due to the focus size of the X-ray source 101. The calculation is performed on the X-rays having a width of a sum of the width Ga8 of the transparent objects and the width Gb8 of the opaque objects.

In the present example, the calculation is performed on an X-ray imaging apparatus which uses the grating 103$h$ having aluminum with a width of 75 μm and a thickness of 400 μm as the transparent objects and lead with a width of 25 μm and a thickness of 400 μm as the opaque objects and an X-ray source that has a focus size of 50 μm and generates cone beam X-rays. In the X-ray imaging apparatus of the present example, the X-ray source is arranged at a position at which the focused position of the grating is located when the focused position is rotated by 8 degrees around an intersection point of the surface of the grating and the optical axis, L1 is 1 m, and L2 is 80 cm. FIG. 13 shows an intensity distribution of one discrete X-ray beam using a solid line.

As a comparative example, the calculation is similarly performed on an X-ray imaging apparatus which uses a grating having aluminum with a width of 34 μm and a thickness of 400 μm as the transparent objects and lead with a width of 66 μm and a thickness of 400 μm as the opaque objects and an X-ray source that has a focus size of 50 μm and generates cone beam X-rays. In the X-ray imaging apparatus of the comparative example, the X-ray source is arranged at the focused position of the grating, L1 is 1 m, and L2 is 80 cm. The calculation result is shown by a dashed line in FIG. 13. FIG. 13 shows that the solid line and the dashed line substantially correspond to each other, so that it is known that a discrete X-ray beam having a width smaller than that of the transparent objects can actually be formed by using the present invention.

Although the embodiments of the present invention have been described, the present invention is not limited to these embodiments, and various changes and modifications are possible within the scope of the invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-282233, filed Dec. 17, 2010, which is hereby incorporated by reference herein in its entirety.

INDUSTRIAL APPLICABILITY

The present invention can be used in an imaging apparatus of a sample, which uses a phase change generated when X-rays pass through the sample.

REFERENCE SIGNS LIST

101 X-ray source generating cone beam X-rays
102 cone beam X-rays
103 ($a$ to $h$) grating
104 sample
105 ($a$ to $h$) discrete X-ray beam
106 detector
107 calculation device
108 unit for moving/rotating grating
111 optical axis
112 center line of grating
113 extended line of center line of opaque objects
114 ($a$ to $h$) transparent objects
115 ($a$ to $h$) opaque objects
116 ($a$ to $c$) focused position of grating

The invention claimed is:

1. An X-ray imaging apparatus comprising:
an X-ray source;
a grating configured to divide diverging X-rays irradiated from the X-ray source; and
a detector configured to detect X-rays which are divided by the grating and pass through a sample,
wherein the grating includes a plurality of transparent objects which pass the diverging X-rays, and a plurality of opaque objects which shield the diverging X-rays,
wherein the plurality of opaque objects which shield the diverging X-rays is arranged so that a plurality of extended lines intersects each other, each of the extended lines being formed by extending a center line, which connects a center of an X-ray source side of each of the plurality of opaque objects facing the X-ray source with a center of a detector side of each of the plurality of opaque objects facing the detector, toward the X-ray source, and
wherein the grating is arranged so that a focused position of the grating at which the plurality of extended lines intersects each other and the X-ray source are arranged at positions different from each other.

2. The X-ray imaging apparatus according to claim 1, wherein the grating is arranged so that a position obtained by moving a position at which the X-ray source is located in a direction perpendicular to an optical axis corresponds to the focused position of the grating.

3. The X-ray imaging apparatus according to claim 1, wherein the grating is arranged so that a position obtained by rotating a position at which the X-ray source is located around one point on an optical axis corresponds to the focused position of the grating.

4. The X-ray imaging apparatus according to claim 1, wherein
when an angle between the center line of the each of the plurality of opaque objects and X-rays entering each of the plurality of opaque object is θ,
θ is greater than 0 degree and smaller than 20 degrees.

5. The X-ray imaging apparatus according to claim 4, wherein the θ is greater than 1 degree and smaller than 15 degrees.

6. The X-ray imaging apparatus according to claim 1, wherein
X-rays entering the grating are shielded by a side surface of each of the plurality of opaque objects, so that
a width of all X-rays divided by the grating on a surface of the grating facing the detector is smaller than a width of the transparent object on a surface of the grating facing the X-ray source.

7. An X-ray imaging apparatus comprising:
an X-ray source;
a grating configured to divide parallel X-rays irradiated from the X-ray source; and
a detector configured to detect intensity of X-rays which are divided by the grating and pass through a sample,
wherein the grating includes a plurality of transparent objects which pass the parallel X-rays and a plurality of opaque objects configured to shield the parallel X-rays, and an angle between a center line which connects a center of each side of each of the plurality of opaque objects facing the X-ray source and facing the detector, and X-rays entering the opaque object is greater than 0 degrees and smaller than 20 degrees, and
wherein, when an aperture ratio of the grating is defined as a formula described below, the aperture ratio is greater than or equal to 5% and smaller than 50%:

$$D = (Ga - t \times \tan\theta)/(Ga + Gb)$$

here, D is the aperture ratio, Ga is a width of the transparent object on a surface of the grating facing the X-ray source, t is a thickness of the grating, Gb is a width of the opaque object on a surface of the grating facing the X-ray source, and θ is an angle between the center line of the opaque object and X-rays entering the opaque object.

8. The X-ray imaging apparatus according to claim 7, wherein an angle between the center line and the X-rays entering the opaque object is greater than 1 degree and smaller than 15 degrees.

9. The X-ray imaging apparatus according to claim 1, wherein
when an aperture ratio of the grating is defined as a formula described below, the aperture ratio is greater than or equal to 5% and smaller than 50%:

$$D = (Ga - t \times \tan\theta)/(Ga + Gb)$$

here, D is the aperture ratio, Ga is a width of the transparent object on a surface of the grating facing the X-ray source, t is a thickness of the grating, Gb is a width of the opaque object on a surface of the grating facing the X-ray source, and θ is an angle between the center line of the opaque object and X-rays entering the opaque object.

10. The X-ray imaging apparatus according to claim 1, wherein X-ray beams are formed on the detector by the divide of the X-rays by the grating.

11. The X-ray imaging apparatus according to claim 1, wherein the sample is placed between the grating and the detector.

12. The X-ray imaging apparatus according to claim 10 further comprising
a calculation device configured to perform calculation based on a detection result of the detector, wherein
the calculation device calculates an amount of positional shift of the X-ray beams on the detector caused by the sample.

13. The X-ray imaging apparatus according to claim 1, wherein a width of the plurality of opaque objects is larger than a width of the plurality of transparent objects.

14. The X-ray imaging apparatus according to claim 7, wherein X-ray beams are formed on the detector by the divide of the X-rays by the grating.

15. The X-ray imaging apparatus according to claim 14, further comprising
a calculation device configured to perform calculation based on a detection result of the detector, wherein
the calculation device calculates an amount of positional shift of the X-ray beams on the detector caused by the sample.

16. The X-ray imaging apparatus according to claim 7, wherein a width of the plurality of opaque objects is larger than a width of the plurality of transparent objects.

17. The X-ray imaging apparatus according to claim 1, wherein the grating is a focused grid.

18. The X-ray imaging apparatus according to claim 1, wherein when an angle between the center line of the each of the plurality of opaque objects and X-rays entering each of the plurality of opaque object is θ,
θ is greater than 0 degree.

19. The X-ray imaging apparatus according to claim 1, wherein the grating is two-dimensional grating.

* * * * *